United States Patent
Rynerson (12)

(10) Patent No.: US 11,083,621 B2
(45) Date of Patent: *Aug. 10, 2021

(54) INSTRUMENT FOR TREATING AN OCULAR DISORDER

(71) Applicant: BlephEx, LLC, Franklin, TN (US)

(72) Inventor: James M. Rynerson, Franklin, TN (US)

(73) Assignee: BLEPHEX, LLC, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/590,228

(22) Filed: Oct. 1, 2019

(65) Prior Publication Data
US 2020/0030146 A1    Jan. 30, 2020

Related U.S. Application Data

(63) Continuation of application No. 16/352,758, filed on Mar. 13, 2019, now Pat. No. 10,449,087, which is a continuation of application No. 13/949,365, filed on Jul. 24, 2013, which is a continuation-in-part of application No. 13/556,729, filed on Jul. 24, 2012, now Pat. No. 9,039,718.

(51) Int. Cl.
*A61F 9/007*    (2006.01)
*A61F 13/38*    (2006.01)

(52) U.S. Cl.
CPC .......... *A61F 9/00709* (2013.01); *A61F 13/38* (2013.01)

(58) Field of Classification Search
CPC ...... A61F 9/00; A61F 9/0008; A61F 9/00709; A61F 9/00736; A61F 9/00745; A61F 9/00772; A61F 13/38; A61H 2205/024

USPC ...................................... 604/1, 294; 606/162
See application file for complete search history.

(56) References Cited

U.S. PATENT DOCUMENTS

| | | |
|---|---|---|
| 111,265 A | 1/1871 | Shoemaker et al. |
| 1,100,504 A | 6/1914 | Taft |
| 1,554,317 A | 9/1925 | Worthing et al. |
| 1,707,353 A | 4/1929 | James et al. |

(Continued)

FOREIGN PATENT DOCUMENTS

| | | |
|---|---|---|
| CA | 2257040 A1 | 6/2000 |
| CN | 86204490 U | 4/1987 |

(Continued)

OTHER PUBLICATIONS

"Connector standard sheets." Wikipedia. < http://en.wikipedia.org/wiki/IEC_60320. Accessed Sep. 13, 2018.

(Continued)

*Primary Examiner* — Martin T Ton
(74) *Attorney, Agent, or Firm* — Wilson Sonsini Goodrich & Rosati

(57) ABSTRACT

An instrument for removing debris from an eye during the treatment of an ocular disorder has a swab and a rigid member. The swab includes a tip portion sized to provide access to the debris on an eyelid of the eye. The rigid member has a distal end portion affixed to the swab and a proximal end portion with a cross-sectional member profile. The cross-sectional member profile is non-circular and has a first groove. The first groove extends longitudinally along the proximal end portion for cooperating with a chuck such that rotation of the proximal end portion within the chuck is inhibited.

18 Claims, 4 Drawing Sheets

(56) References Cited

U.S. PATENT DOCUMENTS

| | | | |
|---|---|---|---|
| 1,832,554 | A | 11/1931 | Holstein et al. |
| 2,006,539 | A | 7/1935 | DeFord |
| 2,546,061 | A | 3/1951 | De et al. |
| 2,766,471 | A | 10/1956 | McKenzie et al. |
| 2,766,650 | A | 10/1956 | Capra et al. |
| 3,029,672 | A | 4/1962 | Lowenborg |
| 3,507,508 | A | 4/1970 | Andrews et al. |
| 3,517,754 | A | 6/1970 | Robert |
| D262,739 | S | 1/1982 | Norman |
| D286,438 | S | 10/1986 | Philip |
| 4,778,457 | A | 10/1988 | York |
| 4,838,851 | A | 6/1989 | Shabo |
| 4,883,454 | A | 11/1989 | Hamburg |
| D306,347 | S | 2/1990 | Robert |
| 4,913,682 | A | 4/1990 | Shabo |
| 4,955,896 | A | 9/1990 | Freeman |
| 5,176,694 | A | 1/1993 | Price |
| 5,456,265 | A | 10/1995 | Yim |
| 5,458,427 | A | 10/1995 | Simond |
| 5,498,077 | A | 3/1996 | Krzywdzjak et al. |
| 5,588,497 | A | 12/1996 | Thorburn |
| 5,632,756 | A | 5/1997 | Kruglick |
| 5,690,618 | A | 11/1997 | Smith et al. |
| D401,332 | S | 11/1998 | George |
| 5,904,390 | A | 5/1999 | Emery et al. |
| 5,974,615 | A | 11/1999 | Schwarz-Hartmann et al. |
| 6,036,198 | A | 3/2000 | Kramer |
| 6,116,900 | A | 9/2000 | Ostler |
| 6,536,066 | B2 | 3/2003 | Dickie |
| 7,384,405 | B2 | 6/2008 | Rhoades |
| D588,697 | S | 3/2009 | Hickok |
| D589,620 | S | 3/2009 | Hickok |
| D645,140 | S | 9/2011 | Peuker et al. |
| D701,304 | S | 3/2014 | Lair et al. |
| D701,308 | S | 3/2014 | Brannon |
| D705,426 | S | 5/2014 | Fiorina et al. |
| 9,039,718 | B2 | 5/2015 | Rynerson |
| 9,675,516 | B2 | 6/2017 | Parsloe |
| 2004/0067098 | A1 | 4/2004 | Sun |
| 2004/0172035 | A1 | 9/2004 | Parmigiani |
| 2005/0132513 | A1 | 6/2005 | Eliav et al. |
| 2006/0116355 | A1 | 6/2006 | Van |
| 2007/0016255 | A1 | 1/2007 | Korb et al. |
| 2007/0049860 | A1 | 3/2007 | Seminara |
| 2007/0060988 | A1* | 3/2007 | Grenon .......... A61F 9/00 607/96 |
| 2007/0231353 | A1 | 10/2007 | Gilbard et al. |
| 2008/0188877 | A1 | 8/2008 | Hickingbotham |
| 2008/0221533 | A1 | 9/2008 | Matityahu |
| 2008/0260563 | A1 | 10/2008 | Refenius et al. |
| 2009/0112242 | A1 | 4/2009 | Kao |
| 2009/0124985 | A1* | 5/2009 | Hasenoehrl .......... A45D 34/04 604/289 |
| 2010/0256552 | A1 | 10/2010 | Korb et al. |
| 2011/0137214 | A1 | 6/2011 | Korb et al. |
| 2011/0144562 | A1 | 6/2011 | Heeren et al. |
| 2011/0160635 | A1 | 6/2011 | Baschnagel |
| 2012/0065556 | A1 | 3/2012 | Smith et al. |
| 2013/0058710 | A1 | 3/2013 | Fan |
| 2013/0081518 | A1 | 4/2013 | Scheid et al. |
| 2013/0331768 | A1* | 12/2013 | Nichamin .......... A61P 29/00 604/22 |
| 2014/0031845 | A1 | 1/2014 | Rynerson |
| 2014/0052164 | A1 | 2/2014 | Rynerson |
| 2014/0214062 | A1 | 7/2014 | Rynerson et al. |
| 2014/0221908 | A1 | 8/2014 | Sonsino et al. |
| 2014/0249509 | A1* | 9/2014 | Rubinfeld .......... A61F 9/0008 604/521 |
| 2019/0209373 | A1 | 7/2019 | Rynerson |

FOREIGN PATENT DOCUMENTS

| | | |
|---|---|---|
| CN | 2538310 Y | 3/2003 |
| CN | 201168118 Y | 12/2008 |
| CN | 201362154 Y | 12/2009 |
| CN | 201505215 U | 6/2010 |
| CN | 201692153 U | 1/2011 |
| JP | H06261839 A | 9/1994 |
| JP | H10108801 A | 4/1998 |
| WO | WO-9633676 A1 | 10/1996 |
| WO | WO-2009066077 A1 | 5/2009 |
| WO | WO-2010149959 A1 | 12/2010 |
| WO | WO-2012092320 A2 | 7/2012 |
| WO | WO-2012092320 A3 | 9/2012 |
| WO | WO-2014018651 A1 | 1/2014 |

OTHER PUBLICATIONS

Advertising material for the AlgerBrush II. Bates No. PPM000709-PPM000710. 2 pages.

Alger Equipment Company, Algerbrush II, Introduction, Product Info, About Us, FAQ's, [https://web.archive.org/web/20101121065649/http://www.algercompany.co] (2009)]; [https://web.archive/org/web/20100103204839/http://www.algercompany.co](2009); [https://web.archive.org/web/20100817072535/http://www//algercompany.co] (2009); [https://web.archiveorg/web20101030135414/http://www.algercompany.co] (2009); [https://web.archive.org/web/20101029151415/http://www.algercompany.co] (2009); and [https://web/archive.org/web/20101030135409/http://].

Algerbrush II Quick Reference Catalog, [cited Oct. 2012]. Available from [www.rheinmedical.com/wpcontent/uploads/2012/10/AlgerbrushCatalog1333AHBC.pdf].

Australian Patent Application No. 2013295781 Office Action dated Sep. 20, 2017.

Blephex LLC v. Pain Point Medical Systems, Inc., d/b/ MiBo Medical Group Inc., Case No. 3:16-cv-00410N, USDC, Northern District of Texas, Dallas Division, Defendant's Amended Invalidity Contentions, filed Oct. 11, 2018. 59 pages.

Blephex LLC v. Pain Point Medical Systems, Inc., d/b/a MiBo Medical Group Inc, Case No. 3:16-cv-00410N, USDC, Northern District of Texas, Dallas Division, Defendant's Invalidity Contentions, filed Jun. 24, 2016, 15 pages.

Blephex LLC v. Pain Point Medical Systems, Inc., d/b/a MiBo Medical Group Inc., Case No. 3:16-cv-00410N, USDC, Northern District of Texas, Dallas Division, Claim Construction Order, Issued Apr. 23, 2019. 12 pages.

Brown et al.: Corneal Rust Removal by Electric Drill. British J. Ophthal. 59: 586-589 (1975). Bates No. PPM002809-PPM002813. 5 pages.

Canadian Patent Application No. 2,873,219 Office Action dated Mar. 21, 2016.

Chinese Patent Application No. 201380049077.1 Office Action dated Dec. 28, 2015 (English Translation Available).

Eurasian Patent Application No. 201590259 Office Action dated Jul. 11, 2017 (English Translation Only).

Eurasian Patent Application No. 201590259 Office Action dated Oct. 4, 2016 (English Translation Available).

European search report with written opinion dated Mar. 26, 2019 for EP Application No. 18185867.

Forthemoney et al., Blepharitis, 6 pages. [cited 2012 Mar. 2012]. Available from [http://en.wikipedia.org/w/index.php?oldid=474399644].

Geerling G., et al., The International Workshop on Meibomian Gland Dysfunction: Report of the Subcommittee on Management and Treatment of Meibomian Gland Dysfunction. The Association for Research in Vision and Ophthalmology, Inc., IOVS Special Issue 2011, 52.4 (2011): 2050-2064.

Greiner, et al. Effects of eyelid scrubbing on the lid margin. CLAO J. Apr. 1999;25(2):109-13.

Japanese Patent Application No. 2015-524423 Office Action dated May 15, 2017 (English Translation Only).

Key., A Comparative Study of Eyelid Cleaning Regimens in Chronic Blepharitis. Contact Lens Association of Opthalmologists Journal, 22.3 (Jul. 1996): 209-212.

Knop et al., The International Workshop on Meibomian Gland Dysfunction: Report of the Subcommittee on Anatomy, Physiology,

(56) References Cited

OTHER PUBLICATIONS and Pathophysiology of the Meibomian Gland. The Association for Research in Vision and Ophthalmology, Inc., IOVS Special Issue 2011, 52.4 (2011): 1938-1978.
Myco Ind., Inc., v. Blephex, LLC, Case No. 2:19-cv-10645, USDC, Eastern District of Michigan, Southern Division, Opinion and Order Granting Plaintiffs Amended Motion for Preliminary Injunction, issued Aug. 27, 2019. 24 pages.
OCuSOFT [cited Jan. 8, 2015]. Available from: [http://www.ocusoft.com/Foreign-body-Removai-AKGERBRUSH-II-CHUCK-P4666.aspx] Screen capture of page submitted herewith as Algerbrush II Chuck with bilobal fitting.
PCT/US2013/051850 International Search Report and Written Opinion dated Oct. 14, 2013.
Rhein Medical, Inc., [cited Jan. 8, 2015]. Retrieved form the internet at [http://www.rheinmedical.com/ products-page/algerbrushes/08-13154-algerbrush-ii-chuch-2-5mm-round-fine-gruit-diamond-ball//] Screen capture of page submitted herewith as Algerbrush II chuck and round burr.
Stevens., How to Clean Eyelids. Community Eye Health Journal, 24.75 (Sep. 2011): 15 pages.
The Alger Co., Inc., [cited Dec. 22, 2014]. Available from [http://www.algercompany.com/brush/pdf-file/], click on "Operating/Sterilization Procedures" then click on "Algerbrush II Operating Instruction Rev. 3 2012" to retrieve pdf submitted herewith as "Aigerbrush-11-Operating_instruct. 2012".
The Alger Co., Inc., [cited Dec. 22, 2014]. Available from [http://www.algrecompany.com/brush/2013/01/02/lhe-algerbrush-ii-2/] Screen capture of page submitted herewith as Algerbrush II Product Page.
The Alger Company, Alger Brush Product Information, 2 pages. [cited 2012]. Available from [http://www.algercompany.com/brush.product-info].
The Alger Company, AlgerBrush II Operating Instructions, Apr. 2012, 2 pages.
The Alger Company, AlgerBrush Product Spec Sheet, Jun. 24, 2012, 1 page.
The Alger Company, Inc., AigerBrush II, 1 page. [cited Mar. 30, 2012]. Available from [http://www.algercompany.com/download/ab_web/Algerbrush3_8.pdf].
BlephEx, LLC. v. Myco Industries, Inc. and John R. Choate. Civil Action No. 2:19-cv-13089. BlephEx, LLC's Motion for a Preliminary Injunction and Brief in Support. Nov. 7, 2019.
BlephEx, LLC. v. Myco Industries, Inc. and John R. Choate. Civil Action No. 2:19-cv-13089. BlephEx, LLC's Reply in Further Support of Motion for a Preliminary Injunction. Dec. 11, 2019.
BlephEx, LLC. v. Myco Industries, Inc. and John R. Choate. Civil Action No. 2:19-cv-13089. Declaration of Dr. James M. Rynerson in Support of BlephEx, LLC's Motion for a Preliminary Injunction. Nov. 7, 2019.
BlephEx, LLC. v. Myco Industries, Inc. and John R. Choate. Civil Action No. 2:19-cv-13089. Declaration of Matthew D. Robson in Support of BlephEx, LLC's Motion for a Preliminary Injunction. (Including the following Exhibits 1-30, 32-62). Nov. 7, 2019.
Exhibit 1: A true and correct U.S. Pat. No. 10,449,087. Nov. 7, 2019.
Exhibit 2: A true and correct excerpted prosecution history of U.S. Pat. No. 10,449,087. Nov. 7, 2019.
Exhibit 3: A true and correct excerpted U.S. Appl. No. 13/556,729. Nov. 7, 2019.
Exhibit 4: A true and correct U.S. Pat. No. 9,039,718. Nov. 7, 2019.
Exhibit 5: A true and correct Final Written Decision of the Patent Trial and Appeal Board of the United States Patent and Trademark Office regarding U.S. Pat. No. 9,039,718, dated Feb. 28, 2018. Nov. 7, 2019.
Exhibit 6: A true and correct excerpted Myco Industries, Inc.'s ("Myco") Mar. 15, 2019 Motion for Preliminary Injunction from Myco Industries, Inc. v. BlephEx, LLC, 2:19-cv-10645-GAD-EAS, (E.D. Mich.). Nov. 7, 2019.
Exhibit 7: A true and correct Court's Aug. 27, 2019 Order regarding Myco's Motion for Preliminary Injunction from Myco Industries, Inc. v. BlephEx, LLC, 2:19-cv-10645-GAD-EAS, (E.D. Mich.). Nov. 7, 2019.
Exhibit 8: A true and correct Myco's Oct. 3, 2019 Opening Claim Construction Brief from Myco Industries, Inc. v. BlephEx, LLC, 2:19-cv-10645-GAD-EAS, (E.D. Mich.). Nov. 7, 2019.
Exhibit 9: A true and correct BlephEx's Oct. 3, 2019 Opening Claim Construction Brief from Myco Industries, Inc. v. BlephEx, LLC, 2:19-cv-10645-GAD-EAS, (E.D. Mich.). Nov. 7, 2019.
Exhibit 10: A true and correct excerpted Declaration of Dr. Penny Asbell submitted in support of BlephEx's proposed claim constructions, dated Aug. 29, 2019, from Myco Industries, Inc. v. BlephEx, LLC, 2:19-cv-10645-GAD-EAS (E.D. Mich.). Nov. 7, 2019.
Exhibit 11: A true and correct excerpted transcript of the Sep. 11, 2019 deposition of Dr. Steve Silberberg from Myco Industries, Inc. v. BlephEx, LLC, 2:19-cv-10645-GAD-EAS (E.D. Mich.). Nov. 7, 2019.
Exhibit 12: A true and correct Exhibit 14 to the Sep. 11, 2019 deposition of Dr. Steve Silberberg from Myco Industries, Inc. v. BlephEx, LLC, 2:19-cv-10645-GAD-EAS (E.D. Mich.). Nov. 7, 2019.
Exhibit 13: A true and correct excerpted Dorland's Illustrated Medical Dictionary, 30th Ed. (2003). Nov. 7, 2019.
Exhibit 14: A true and correct web page titled "What Makes up the Eyelid Margin?" dated Jan. 29, 2014 from the website of the American Academy of Ophthalmology. Nov. 7, 2019.
Exhibit 15: A true and correct web page titled "Eyelid margin" from the website of the American Academy of Ophthalmology. Nov. 7, 2019.
Exhibit 16: A true and correct article by Nelson et al. titled "The International Workshop on Meibomian Gland Dysfunction: Report of the Definition and Classification Subcommittee" by (2011) downloaded from iovs.arvojournals.org. Nov. 7, 2019.
Exhibit 17: A true and correct excerpted Chapter 1, Eyelid Anatomy, of a book by A. Biswas titled "Eyelid Tumors" (2014). Nov. 7, 2019.
Exhibit 18: A true and correct excerpted Myco's Answer to Amended Counterclaims from Myco Industries, Inc. v. BlephEx, LLC, 2:19-cv-10645-GAD-EAS, (E.D. Mich.). Nov. 7, 2019.
Exhibit 19: A true and correct document titled Owner's Manual for the BlephEx product. Nov. 7, 2019.
Exhibit 20: A true and correct document titled Instructions for Use for the AB Max product. Nov. 7, 2019.
Exhibit 21: A true and correct FDA web page relating to the AB Max product. Nov. 7, 2019.
Exhibit 22: A true and correct FDA web page describing the Product Code PYU. Nov. 7, 2019.
Exhibit 23: A true and correct Myco's web page www.ab-max.com/doctors/. Nov. 7, 2019.
Exhibit 24: A true and correct Myco's web page at www.alc-max.com/doctors/how-it-works/. Nov. 7, 2019.
Exhibit 25: A true and correct Myco's web page at www.ab-max.com/doctors/increase-profits/. Nov. 7, 2019.
Exhibit 26: A true and correct BlephEx's web page at www.blephex.com/doctors/index.php. Nov. 7, 2019.
Exhibit 27: A true and correct BlephEx's web page at www.blephex.com/doctors/index.php/how-does-blephex-work.html. Nov. 7, 2019.
Exhibit 28: A true and correct web page titled "BlephEx Treatment Offered in More Than 1,000 Ophthalmic Practices Worldwide" dated Apr. 28, 2015, at https://www.prnewswire.com/news-releases/blephex-treatment-offered-in-more-than-1000-ophthalmic-practices-worldwide-300073037.html. Nov. 7, 2019.
Exhibit 29: A true and correct web page titled "AOP Awards 2017 Product of the Year" at https://www.aop.org.uk/education-and-events/aop-awards/previous- years/2017/product-of-the-year#Scope. Nov. 7, 2019.
Exhibit 30: A true and correct Myco's advertisement document named "Trade In Trade Up." Nov. 7, 2019.
Exhibit 32: A true and correct capture of Myco's Facebook page, captured on Oct. 27, 2019. Nov. 7, 2019.
Exhibit 33 is a true and correct document reflecting a web page post from Philip Wren. Nov. 7, 2019.

(56) References Cited

OTHER PUBLICATIONS

Exhibit 34 is a true and correct document reflecting a web page post from Steve Silberberg. Nov. 7, 2019.
Exhibit 35: Redacted. Nov. 7, 2019.
Exhibit 36: Redacted. Nov. 7, 2019.
Exhibit 37: Redacted. Nov. 7, 2019.
Exhibit 38: Redacted. Nov. 7, 2019.
Exhibit 39: Redacted. Nov. 7, 2019.
Exhibit 40: Redacted. Nov. 7, 2019.
Exhibit 41: Redacted. Nov. 7, 2019.
Exhibit 42: Redacted. Nov. 7, 2019.
Exhibit 43: Redacted. Nov. 7, 2019.
Exhibit 44: Redacted. Nov. 7, 2019.
Exhibit 45: Redacted. Nov. 7, 2019.
Exhibit 46: Redacted. Nov. 7, 2019.
Exhibit 47: A true and correct Myco's web page at www.ab-max.com/doctors/. Nov. 7, 2019.
Exhibit 48: A true and correct Court's Opinion and Order Denying Defendants' Motion to Dismiss from *Myco Industries, Inc. v. BlephEx, LLC*, 2:19-cv-10645-GAD-EAS, (E.D. Mich.). Nov. 7, 2019.
Exhibit 49: A true and correct opinion titled *Johns Hopkins Univ. v. Alcon Labs.*, No. 15-525, 2018 U.S. Dist. Lexis 70403 (D. Del. Mar. 1, 2018). Nov. 7, 2019.
Exhibit 50: A true and correct Mr. John E. Nemazi's Jun. 14, 2019 letter to me. Nov. 7, 2019.
Exhibit 51: A true and correct excerpted Myco's Response Brief Opposing Defendants' Motion to Dismiss from *Myco Industries, Inc. v. BlephEx, LLC*, 2:19-cv-10645-GAD-EAS, (E.D. Mich.). Nov. 7, 2019.
Exhibit 52: A true and correct excerpted Myco's Amended Motion for Preliminary Injunction from *Myco Industries, Inc. v. BlephEx, LLC*, 2:19-cv-10645-GAD-EAS, (E.D. Mich.). Nov. 7, 2019.
Exhibit 53: A true and correct Exhibit 1 (Declaration of John Choate) to the Myco's Amended Motion for Preliminary Injunction from *Myco Industries, Inc. v. BlephEx, LLC*, 2:19-cv-10645-GAD-EAS, (E.D. Mich.). Nov. 7, 2019.
Exhibit 54: A true and correct opinion titled *Brocade Comm. Sys., Inc. v. A10 Networks, Inc.*, No. C 10-3428 PSG, 2013 WL 140039 (N.D. Cal. 2013). Nov. 7, 2019.
Exhibit 55: A true and correct opinion titled *Metso Minerals, Inc. v. Powerscreen Intern. Distribution Ltd.*, No. 06-cv-1446 (ADS)(ETB), 2011 WL 2149629 (E.D.N.Y. May 26, 2011). Nov. 7, 2019.
Exhibit 56: A true and correct opinion titled Metalcraft of *Mayville, Inc. v. Toro Co.*, No. 16-C-544, 2016 WL 4076894, (E.D. Wis. Aug. 1, 2016). Nov. 7, 2019.
Exhibit 57: A true and correct opinion titled *Cornucopia Prods., LLC v. Dyson, Inc.*, No. 12-234, 2012 WL 3094955 (D. Ariz. Jul. 27, 2012). Nov. 7, 2019.
Exhibit 58: A true and correct document titled Exhibit D—Individual Debtor's Statement of Compliance with Credit Counseling Requirement from in re John Raymond Choate, Jr. et al. (Bankr. E.D. Mich.). Nov. 7, 2019.
Exhibit 59: A true and correct excerpted transcript of the Feb. 1, 2017 deposition of Mr. John Choate from *Rysurg, LLC v. John R. Choate*, No. 2014-CA-000805XXXXMB(AG), Circuit Court of the 15th Judicial Circuit in and for Palm Beach County, Florida. Nov. 7, 2019.
Exhibit 60: A true and correct U.S. Patent Publication No. 2013/0331768. Nov. 7, 2019.
Exhibit 61: A true and correct Settlement Agreement and Release. Nov. 7, 2019.
Exhibit 62: A true and correct Amendment to Settlement Agreement and Release. Nov. 7, 2019.
*Blephex LLC v. Myco Industries, Inc. and John R. Choate*, Case No. 2:19-cv-13089-DML-APP, Exhibit 1, Invalidity Contentions for U.S. Pat. No. 10,449,087, filed Jun. 1, 2020, 21 pages.
*Blephex LLC v. Myco Industries, Inc. and John R. Choate*, Case No. 2:19-cv-13089-DML-APP, Exhibit 2, Invalidity Contentions for U.S. Pat. No. 10,449,087, filed Jun. 1, 2020, 30 pages.
*Blephex LLC v. Myco Industries, Inc. and John R. Choate*, Case No. 2:19-cv-13089-DML-APP, Exhibit 3, Invalidity Contentions for U.S. Pat. No. 10,449,087, filed Jun. 1, 2020, 20 pages.
*Blephex LLC v. Myco Industries, Inc. and John R. Choate*, Case No. 2:19-cv-13089-DML-APP, Exhibit 4, Invalidity Contentions for U.S. Pat. No. 10,449,087, filed Jun. 1, 2020, 21 pages.
*Blephex LLC v. Myco Industries, Inc. and John R. Choate*, Case No. 2:19-cv-13089-DML-APP, Exhibit 5, Invalidity Contentions for U.S. Pat. No. 10,449,087, filed Jun. 1, 2020, 25 pages.
*Blephex LLC v. Myco Industries, Inc. and John R. Choate*, Case No. 2:19-cv-13089-DML-APP, Exhibit 6, Invalidity Contentions for U.S. Pat. No. 10,449,087, filed Jun. 1, 2020, 21 pages.
*BlephEx LLC v. Myco Industries, Inc. and John R. Choate*, Case No. 2:19-cv-13089-GAD-EAS, USDC, Eastern District of Michigan, Defendant's Disclosure of Invalidity Contentions, filed Jun. 1, 2020, 15 pages.
AlgerBrush II device. Bates No. PPM000714-PPM000716. 3 pages. (Oct. 11, 2018).
AlgerBrush II device. Bates No. PPM002763. 1 page. (Oct. 11, 2018).
AlgerBrush II device. Bates No. PPM002764. 1 page. (Oct. 11, 2018).
Blephex Advertisement. Bates No. B000584. 1 page. (Oct. 11, 2018).
Blephex Owner's Manual. Bates No. B000516-6000521. 6 pages. (Oct. 11, 2018).
Cotton swab. Bates No. PPM002765. 1 page. (Oct. 11, 2018).
Dremel brand rotary tool. Bates. No. PPM002766. 1 page. (Oct. 11, 2018).
Dremel brand rotary tool. Bates. No. PPM002767. 1 page. (Oct. 11, 2018).
Dremel brand rotary tool. Bates. No. PPM002768. 1 page. (Oct. 11, 2018).
Dremel brand rotary tool. Bates. No. PPM002769. 1 page. (Oct. 11, 2018).
Dremel brand rotary tool variable speed setting. Bates. No. PPM002770. 1 page. (Oct. 11, 2018).
Dremel Instructional Safety Manual. Bates No. PPM002771-PPM002793. 23 pages. (Oct. 11, 2018).
Dremel Quick Start Book. Bates No. PPM002794-PPM002804. 11 pages. (Oct. 11, 2018).
The Alger Company. Algerbrush and Algerbrush II. Bates No. PPM00283-PPM00292. 10 pages. (Jun. 24, 2016).
Weck-Cel brand surgical sponge. Bates No. PPM002805-PPM002808. 4 pages. (Oct. 11, 2018).

* cited by examiner

INSTRUMENT FOR TREATING AN OCULAR DISORDER

CROSS-REFERENCE TO RELATED APPLICATIONS

This application is a continuation of U.S. application Ser. No. 16/352,758, filed Mar. 13, 2019, now U.S. Pat. No. 10,449,087, issued Oct. 22, 2019, which is a continuation of U.S. application Ser. No. 13/949,365, filed Jul. 24, 2013, which is a continuation-in-part of U.S. application Ser. No. 13/556,729, filed Jul. 24, 2012, now U.S. Pat. No. 9,039,718, issued May 26, 2015, the disclosures of each are hereby incorporated by reference in their entirety.

TECHNICAL FIELD

The present invention relates generally to a method and apparatus for treating an ocular disorder, and more particularly, to treating eyelid margin disease.

BACKGROUND

Ocular disorders such as those relating to eyelid margin disease are particularly common pathological conditions of the ocular adenexa. By way of example, these disorders include blepharitis, meibomitis, and dry eye syndrome. Despite advances in opthamology and medical treatments in general, the recommended treatments for these exemplary common ocular disorders has remained essentially unchanged for decades.

Historically, treatment of eyelid margin disease begins and ends with the patient. The patient first begins to notice symptoms including eyelid redness, flaking of skin on the eyelids, crusting and/or cysts at the eyelid margins, and a gritty sensation of the eye culminating in irritation, burning, and reduced vision. Should these symptoms remain unchanged or worsen, the patient routinely seeks the advice of an eye specialist, such as an ophthalmologist. After carefully considering the patients' medical history and investigating various possible causes, the specialist may prescribe a hygienic home treatment procedure for the patient to perform regularly in conjunction with antibiotics and/or topical steroids until the disease subsides.

The goal of the hygienic home treatment procedure is to remove debris, oil, and scurf that have collected along the eyelid margin during progression of the disorder. Removal of this debris is critical to both healing the eye and preventing a resurgence of the disorder. Without proper, regular removal of accumulated debris, such ocular disorders regularly worsen despite periodic treatments.

Hygienic home treatment of such ocular disorders is generally a two-step process. First, the patient softens the debris and scurf by applying a warm compress, diluted baby shampoo, or a specialized liquid solution to the eyelid margin. This first step is intended to prepare the debris for removal while preventing further irritation to the eye. Second, the patient attempts to remove the debris by physically scrubbing the eyelid margin, the base of the eyelashes, and the pores of the meibomian glands. This scrubbing is routinely attempted with either a generic cotton swab, a fingertip, or a scrub pad placed over the fingertip and applied against the eye. By cleaning debris and scurf free from the base of the eyelashes and unclogging the pores of the meibomian glands, the patient may improve the overall health of the eyelid margin; thereby reducing irritation, burning, and other symptoms related to the disorder.

Unfortunately for many patients, such hygienic home treatment is met with limited success due to the practical difficulties of cleaning one's own eye with an imprecise instrument such as a fingertip or cotton swab. For instance, many patients do not have the necessary dexterity to manipulate their fingertip or a cotton swab along the eyelid margin. Moreover, a shake, tremor, or poor near vision further complicate such self-treatment. Even for those capable of incorporating hygienic home treatment into their daily routine, many, if not most people, are wary of placing objects near their eyes to actively scrub along the eyelid margin. Given this anxiety, discomfort, and the inability to specifically target debris deposits, patients routinely fail to totally cleanse the margin of the eyelid, the base of the eyelashes, and the meibomian glands. While the attempted treatment may temporarily abate the patient's symptoms, subtle continuation of the disease often persists; thus permitting a low-grade inflammation to develop and, ultimately lead to chronic dry eye syndrome. Further, this treatment is typically required to be performed for the rest of the patient's life; thereby, creating a substantial hurdle to regular and effective compliance during hygienic home treatment.

Evidence suggests that medical costs associated with dry eye syndrome, often induced by ocular diseases such as blepharitis, are currently over 68 billion dollars each year. Many of these expenses are needlessly incurred due to the patients' failure to perform regular and effective treatments resulting in increased doctor visits, medications, and artificial tears. These expenses create a significant financial burden for insurance carriers, especially Medicare, which provides primary medical coverage for many individuals particularly prone to dry eye disease, such as the elderly.

There is a need for a method and apparatus for use in treating ocular disorders, such eyelid margin diseases, that addresses present challenges and characteristics such as those discussed above.

SUMMARY

One exemplary embodiment of an instrument for the removal of debris from an eye during the treatment of an ocular disorder has a swab and a rigid member. The swab includes a tip portion sized to provide access to the debris on an eyelid of the eye. The rigid member has a distal end portion and a proximal end portion. The distal end portion of the rigid member is affixed to the swab, and the proximal end portion has a cross-sectional member profile. The cross-sectional member profile of the proximal end portion is non-circular and has a first groove. The first groove extends longitudinally along the proximal end portion for cooperating with a chuck such that rotation of the proximal end portion within the chuck is inhibited.

One exemplary embodiment of a device for the removal of a debris from an eye during the treatment of an ocular disorder has a mechanical drive unit, a chuck, and an instrument. The chuck is connected to and is rotatably driven by the mechanical drive unit. The chuck also has an aperture extending at least partially therethrough with a cross-sectional aperture profile. The instrument is removably secured within the aperture and has a swab and a rigid member. The swab includes a tip portion sized to provide access to the debris on an eyelid of the eye. The rigid member has a distal end portion and a proximal end portion. The distal end portion of the rigid member is affixed to the swab, and the proximal end portion has a cross-sectional member profile configured to cooperate with the cross-sectional aperture profile of the aperture such that rotation of the proximal end portion within the aperture is inhibited. Accordingly, the mechanical drive unit rotatably drives the instrument via the chuck for removing debris.

Various additional objectives, advantages, and features of the invention will be appreciated from a review of the following detailed description of the illustrative embodiments taken in conjunction with the accompanying drawings.

BRIEF DESCRIPTION OF THE DRAWINGS

The accompanying drawings, which are incorporated in and constitute a part of this specification, illustrate embodiments of the invention and, together with a general description of the invention given above, and the detailed description given below serve to explain the invention.

DETAILED DESCRIPTION

Figure 1:
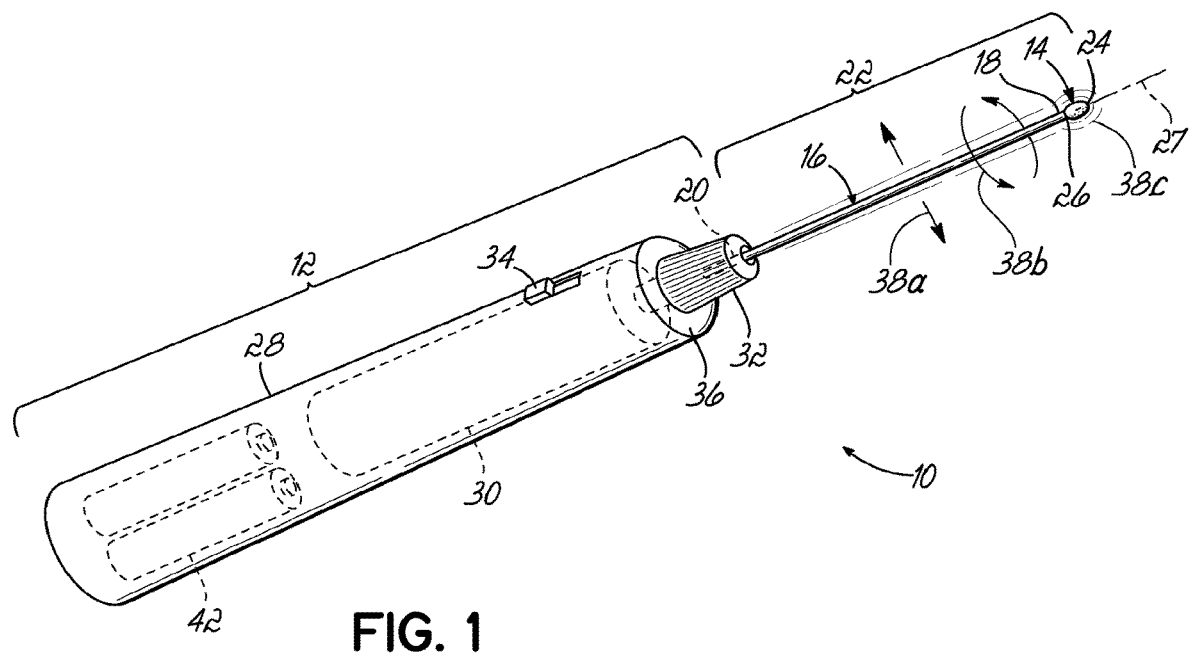
FIG. 1 is a perspective drawing of one embodiment of the device.
Figure 5A:
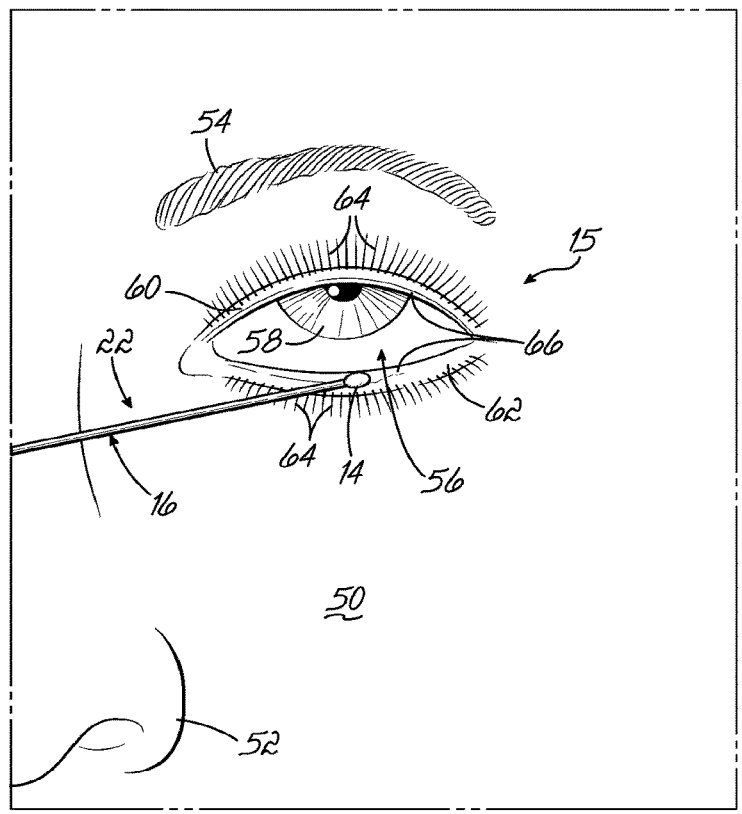
FIG. 5A is a drawing of the device of FIG. 1 treating a lower eyelid margin of an eye.
Figure 5B:
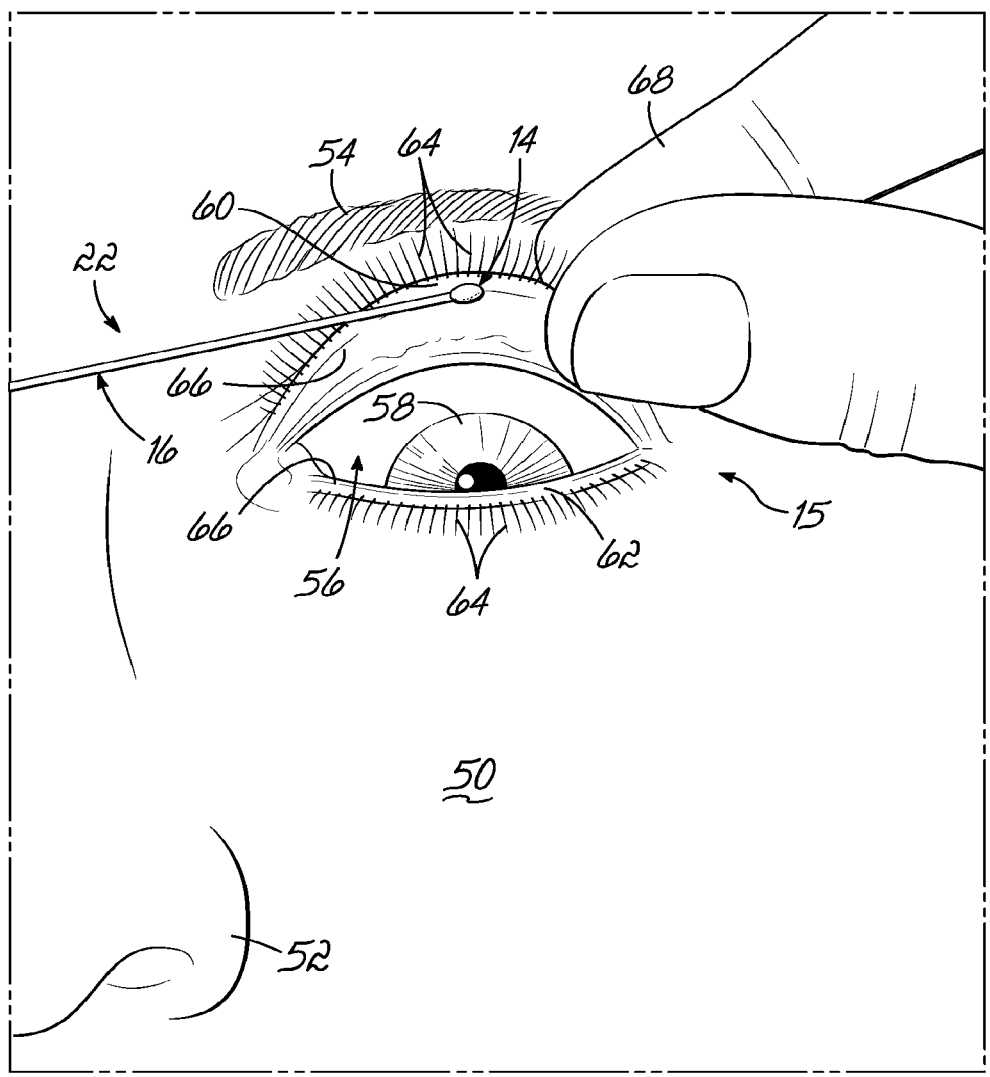
FIG. 5B is a drawing of the device of FIG. 1 treating a upper eyelid margin of an eye.

With reference to FIG. 1, an embodiment of the device 10 for treating an ocular disorder, particularly with respect to eyelid margin diseases, includes a mechanical drive unit 12 which operably moves a swab 14 to facilitate removal of debris from an eye 15 (see FIGS. 5A-5B). The swab 14 is connected to a rigid member 16 having both a distal end portion 18 and a proximal end portion 20. The swab 14 is affixed to the distal end portion 18 of the rigid member 16 to create an instrument 22, which may be secured to the mechanical drive unit 12. As shown in FIG. 1, the proximal end portion 20 is removably secured to the mechanical drive unit 12 in order to transmit motion from the mechanical drive unit 12, through the rigid member 16, and to the swab 14. It will be appreciated that any known method may be used to removably secure the instrument 22 to the mechanical drive unit 12. Moreover, it will also be appreciated that device 10 is not intended to be limited to the instrument 22 being removably secured to the mechanical drive unit 12. For instance, in another embodiment, the rigid member 16 may be either permanently secured or removably secured to either one of the swab 14 and/or the mechanical drive unit 12.

In one aspect of the instrument 22, the swab 14 includes a tip portion 24 and a base portion 26. While the swab 14 may be of a size sufficient to access debris on the eye 15 as shown in FIGS. 1, 5A, and 5B, at least the tip portion 24 is of a size sufficient to access debris on the eye 15. For instance, the swab 14 has an approximate length between 1.0-3.0 millimeters and an approximate width of between 0.5-1.5 millimeters. More particularly, the swab 14 has an approximate length of 2 millimeters and an approximate width of 1 millimeter. It will be appreciated that the swab 14 may be manufactured of any material suitable for contacting the eye 15 without harming the eye 15. However, as shown in the embodiment of FIG. 1, the swab 14 is a sponge. As described herein, "sponge" broadly refers to any material that is soft, porous, and resilient. Particularly, the swab 14 is a medical grade sponge or a surgical grade sponge capable of removing debris from on the eye 15 without harming the eye 15. As shown in the exemplary embodiment of FIG. 1, the swab 14 is a methyl cellulose sponge. It will be appreciated; however, that similar materials capable of removing debris from on the eye 15 without harming the eye 15 are readily apparent and may also be used.

In another aspect of the instrument 22, the rigid member 16 is a plastic, cylindrical shaft including a central axis 27. The shaft extends along the central axis 27 between the mechanical drive unit 12 and the swab 14. The rigid member 16 is sufficiently rigid to effectively transmit motion from the mechanical drive unit 12 to the swab 14. As shown in FIG. 1, the swab 14 is permanently affixed to the distal end portion 18 by forming the base portion 26 to the rigid member 16 during manufacturing. However, it will be appreciated that any known method of affixing the swab 14 to the rigid member 16 may be used. In an exemplary embodiment, any material or shaft shape may be used so long as the rigid member 16 is rigid enough to transmit sufficient motion from the mechanical drive unit 12 to the swab 14 in order to remove debris from on the eye 15.

Furthermore, the mechanical drive unit 12 includes a body 28, an electric motor 30, a chuck 32, and a control switch 34. As such, the device 10 is electromechanical in nature. In an exemplary embodiment, the electric motor 30, the chuck 32, and the control switch 34 are integrated into the body 28 so that the electromechanical device 10 is configured to be handheld as shown in FIG. 1. However, the electromechanical device 10 is not intended to be limited to a handheld configuration, and it will be appreciated that other configurations of the device 10 are readily apparent.

According to the present embodiment, the electric motor 30 is positioned within the body 28. The chuck 32 is operably connected to the electric motor 30 at a forward end portion 36 of the body 28. The proximal end portion 20 of the rigid member 16 is removably secured to the chuck 32. As described herein, the chuck 32 is generally any element capable of removably securing the rigid member 16 to the mechanical drive unit 12. As such, the chuck 32 may be tightened or loosened to respectively secure or remove the instrument 22 to the chuck 32. Thereby, the operable connection of the electric motor 30 transmits a movement 38 through the chuck 32 to the instrument 22. The movement 38 is any motion relative to the mechanical drive unit 12 or, more particularly, to the body 28, that creates relative motion to the debris on the eye 15 such that upon contacting the debris with the swab 14, the debris is removed. As shown, the movement 38 may include, but is not limited to, a reciprocating movement 38a, a rotating movement 38b, or a vibrating movement 38c. The reciprocating movement 38a may be either along the central axis 27 of the rigid member 16 or orthogonal to the central axis 27 of the rigid member 16. In addition, the speed of the movement 38 of the swab 14 is any speed sufficient to remove debris from on the eye 15. It will be appreciated that the speed discussed herein collectively refers to both relative speed of the swab 14 and the frequency of the movement 38 of the swab 14. For instance, the frequency may range from sonic frequencies to ultrasonic frequencies. Furthermore, the speed of the swab 14 may be variable or otherwise selectable such that an operator of the device 10 may select a desirable speed or a forward or reverse direction via the control switch 34.

Moreover, the control switch 34 is operably connected to the electric motor 30 and an electric power source 42 to power the device 10 on and off. In an exemplary embodiment, the electric power source 42 is a battery power source 42 contained within the body 28. The battery power source 42 may be either disposable or rechargeable. The electric power source 42 operably provides electrical power to the electric motor 30, which the operator controls via the control switch 34. It will be appreciated that any known control switch 34 or plurality of control switches 34 may be configured to power the device 10 on and off.

Furthermore, it will be appreciated that the device 10 may be manufactured from various materials suited to specific environments of use. For instance, operators within the professional clinic setting may desire a durable, reusable mechanical drive unit 12 and single-use instruments 22. Some examples of such a professional mechanical drive unit 12 is an Algerbrush I, an Algerbrush II, or similar medical device. However, operators within the home treatment setting may desire the device 10 to be generally disposable and single-use.

Figure 2:
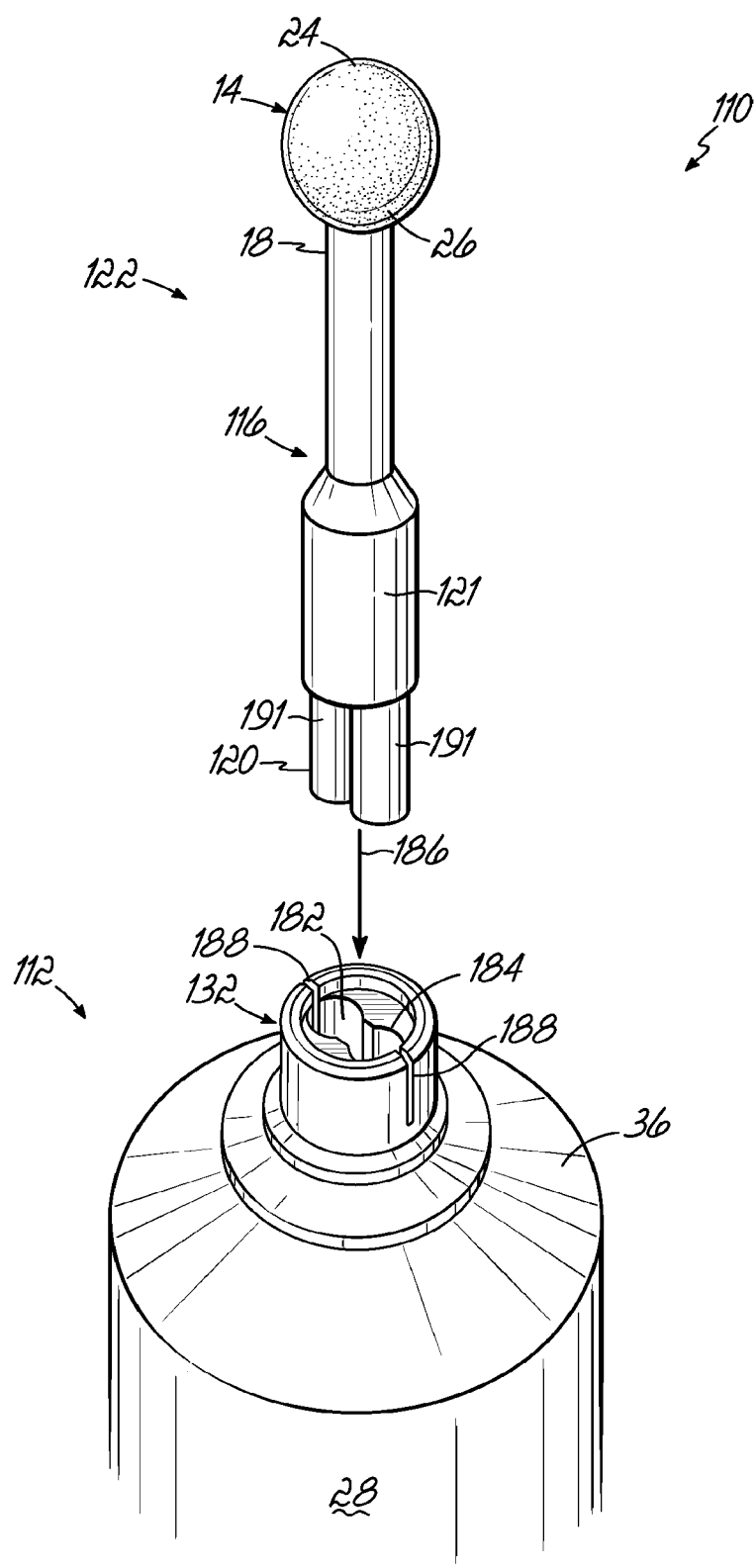
FIG. 2 is a partially exploded perspective view of another embodiment of the device.
Figure 3A:
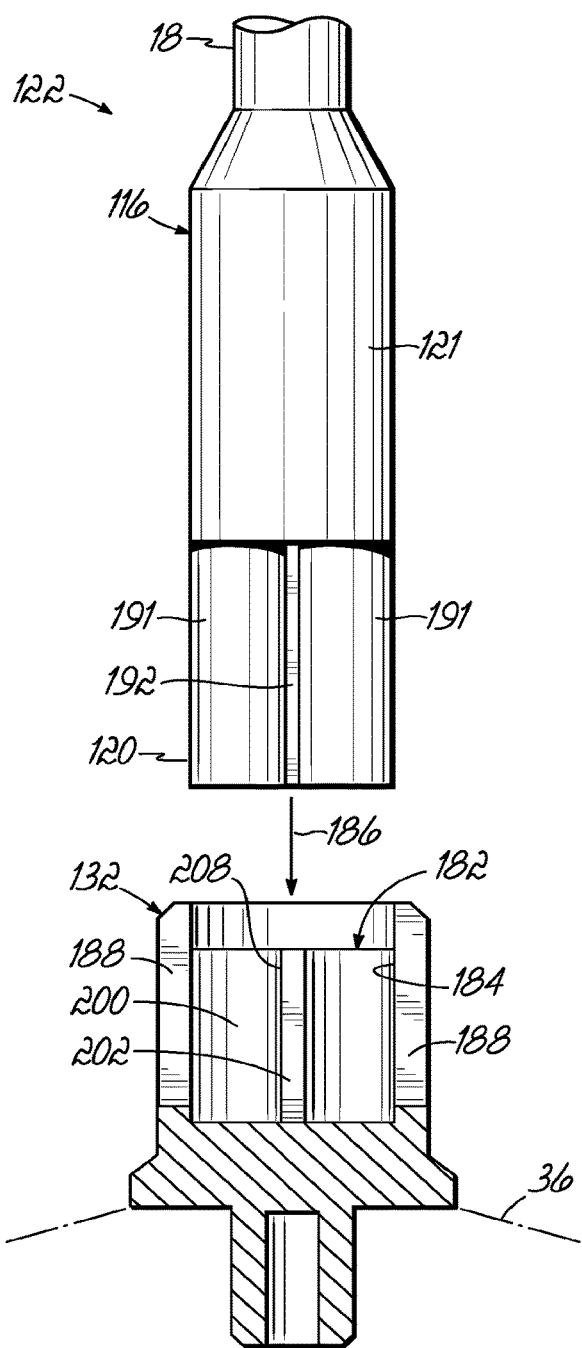
FIG. 3A is an enlarged front view of the device of FIG. 2.
Figure 4:
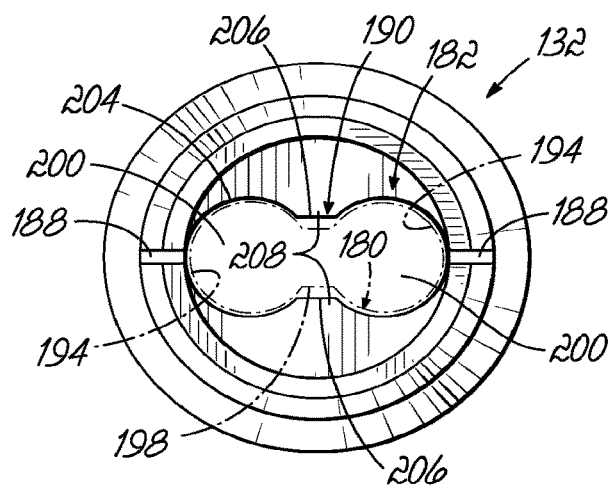
FIG. 4 is a top view of the chuck having a cross-sectional profile of the instrument in phantom lines.
Figure 3B:
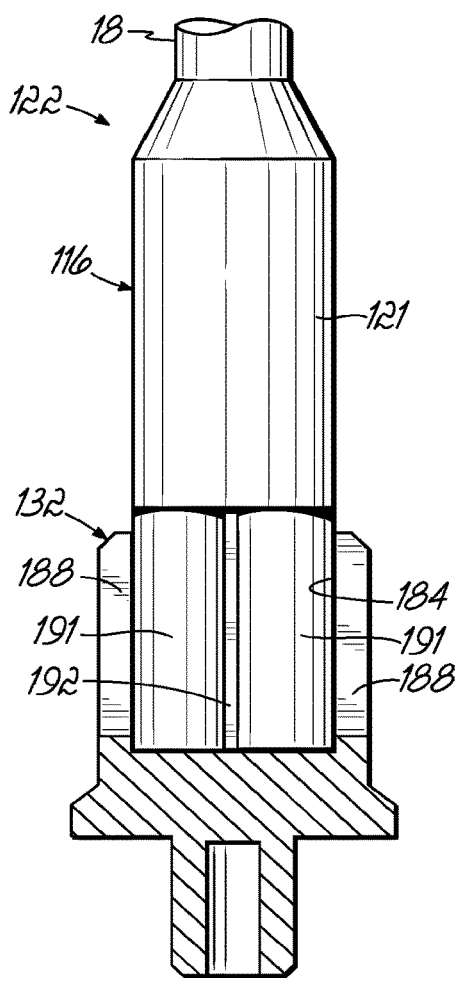
FIG. 3B is an enlarged front view of the device similar to FIG. 3A, but showing an instrument removably secured to a chuck.

FIGS. 2-4 show another embodiment of a device 110 for treating an ocular disorder. The device 110 includes an instrument 122 removably secured to a mechanical drive unit 112. The device 110 provides for safe, simple, and reliable removal and replacement of disposable, single-use instruments 122 between treatments. Specifically, the mechanical drive unit 112 has a chuck 132 projecting from the forward end portion 36 of the body 28 and configured for unique frictional engagement with the instrument 122. In this respect, the attachment between the chuck 132 and the instrument 122 discourages improper installation and inhibits the use of other, unsuitable instruments that may create unnecessary risk of damaging the eye 15 (see FIG. 5A) during use. Moreover, the instrument 122 and chuck 132 provide for simple frictional attachment via insertion and withdrawal (i.e., push-in and pull-out) of the instrument 122 without collars, clasps, or other mechanisms. The chuck 132 also effectively transmits torque to the instrument 122 without generating damaging stress concentrations in either the instrument 122 or the chuck 132. The instrument 122 includes a rigid member 116 having the swab 14 projecting from the distal end portion 18 and, as such, like numbers for the device 110 refer to like features previously described above.

With respect to FIG. 2, the rigid member 116 further includes a proximal end portion 120 sized for insertion into the chuck 132 and an intermediate portion 121 extending between the distal end portion 18 and the proximal end portion 120. The intermediate portion 121 and the distal end portion 18 are both generally cylindrical; however, the intermediate portion 121 has a larger diameter than the distal end portion 18 and tapers toward the distal end portion 18. Also, the proximal end portion 120 has a width that is generally as wide as the diameter of the intermediate portion 121, but a depth generally less than the diameter of the intermediate portion 121 as shown in FIG. 4. However, it will be appreciated that the relative sizes of the portions of the instrument 122, such as diameters, widths, and depths, may vary in accordance with the invention described herein.

With respect to FIGS. 2-4, the proximal end portion 120 has a cross-sectional member profile 180 that inserts into an aperture 182 and frictionally engages a sidewall 184 of the chuck 132 for removably attaching the instrument 122 to the mechanical drive unit 112. Thus, the proximal end portion 120 may be inserted into the aperture 182 as indicated by arrow 186 and withdrawn in the opposite direction to remove the instrument 122 from the chuck 132. The frictional engagement is generally created by the proximal end portion 120 being sized with an interference fit within the aperture 182 against the sidewall 184. However, the engagement is enhanced by a pair of opposing slots 188 extending longitudinally through the sidewall 184. The slots 188 create resiliency within with sidewall 184 that further aid in frictionally engaging the proximal end portion 120 of the instrument 122. In addition, as the aperture 182 receives the proximal end portion 120, the slots 188 vent ambient air from within the aperture 182 to inhibit air pressure buildup that may force the instrument 122 from the chuck 132 after insertion. However, it will be appreciated that other structures may be used to create resiliency and vents. For example, the chuck 132 may be manufactured from a relatively resilient material, and the aperture 182 may include a vent of any shape through another portion of the chuck 132 for releasing air pressure. In an alternative embodiment, the proximal end portion 120 may be removably attached to the chuck 132 via other structures or connectors, such as a collar or clasp. In any case, the invention is not intended to be limited to the exemplary embodiments described herein.

FIGS. 3A-4 show an exemplary embodiment of the cross-sectional member profile 180 defined by the proximal end portion 120 that inserts into the aperture 182, at least a portion of which has a cross-sectional aperture profile 190 for frictionally mating with the cross-sectional member profile 180. The cross-sectional member profile 180 is generally longitudinally uniform along the proximal end portion 120 with a constant cross-section. However, it will be appreciated that the proximal end portion 120 may taper toward the chuck 132 or have another suitable shape for insertion into the aperture 182 in an alternative embodiment.

More particularly, the proximal end portion 120 has a pair of generally parallel cylindrical portions 191 connected by a generally linear tab portion 192 therebetween. As such, the proximal end portion 120 defines the cross-sectional member profile 180 as a pair of curved, opposing major arc surfaces 194 connected by a pair of opposing linear surfaces 196. Accordingly, the generally cylindrical portions 191 at least partially define a groove 198 extending longitudinally along the proximal end portion 120. According to an exemplary embodiment, the linear tab portion 192 and generally cylindrical portions 120 define a pair of opposing grooves 198 extending longitudinally along the proximal end portion 120.

In order to receive the proximal end portion 120 of the instrument 122, the sidewall 184 defines at least a portion of the aperture 182 with the cross-sectional aperture profile 190. As such, the cross-sectional aperture profile 190 has similar, mating surfaces to the cross-sectional member profile 180. The aperture 182 has a pair of generally parallel cylindrical hole portions 200 connected by a generally linear slot portion 202 therebetween. The proximal end portion 120 thus defines the cross-sectional aperture profile 190 as a pair of curved, opposing major arc surfaces 204 connected by a pair of opposing linear surfaces 206. Accordingly, the generally cylindrical hole portions 200 and linear slot portion 202 define a pair of opposing projections 208 extending longitudinally along the sidewalls 184 within the aperture 182.

As the chuck 132 is operatively rotated, the sidewall 184 transmits torque to the proximal end portion 120 and, in turn, rotates the instrument 122. Effectively, each projection 208 is keyed to the respective groove 198 for transmitting the torque. Furthermore, the exemplary embodiment of the cross-sectional aperture profile 190 inhibits insertion of unsuitable instruments while continuing to effectively engage the proximal end portion 120 with many stress-reducing curved surfaces. However, it will be appreciated that the exemplary embodiment of the aperture 182 and the proximal end portion 120 may be other cooperating shapes providing for removable attachment. To the extent other profiles may function similarly to the embodiment described above, it will be appreciated that the exemplary embodiment of the instrument 122 shown in FIGS. 2-4 may have ornamental characteristics, as well.

With respect to FIGS. 5A and 5B, the device 10 is used in a method for treating ocular disorders of the eye 15. While the method for treating ocular disorder will be described with respect to device 10, it will be appreciated that the device 110 (see FIG. 2) may be similarly used. For purposes of describing the environment in which this method occurs, FIGS. 5A and 5B generally show a portion of a face 50 having a nose 52, an eyebrow 54, and the eye 15. The eye 15 described herein generally includes, but is not limited to, an eyeball 56 including a cornea 58, an upper eyelid margin 60, a lower eyelid margin 62, and a plurality of eyelashes 64. In the exemplary embodiment, the device 10 is the swab 14 operably connected to the mechanical drive unit 12 thereby creating the electromechanical device 10 for use in removing debris deposited on at least one of either the upper eyelid margin 60 or the lower eyelid margin 62.

As shown in FIG. 1, an instrument 22 is removably secured to the chuck 132, after which time, the electromechanical device 10 may be powered on and set to a desirable speed by the operator; thereby, the operator effects movement of the swab 14 relative to the electromechanical device 10. Such movement may include, but is not limited to, reciprocating the swab 14 as shown by arrows 38a, rotating the swab 14 as shown by arrow 38b, and/or vibrating the swab 14 as shown by lines 38c. The swab 14 is positioned near the eyeball 56 and along either one of the upper or lower eyelid margins 60, 62 for treatment. In the exemplary embodiment as shown in FIGS. 5A and 5B, the swab 14 moves with constant movement relative to the electromechanical device 10 while near the eyeball 56. Alternatively, it may be desirable to vary the movement of the swab 14 relative to the electromechanical device 10 such that the operator has greater control of treating the ocular disorder.

In an exemplary embodiment, the operator preferably targets the debris present on the eye 15 with the swab 14 of the electromechanical device 10. The debris may be targeted by visually inspecting the eye 15 with or without the aid of a magnification device. Once the debris is targeted, the swab 14 contacts the portion of the eye 15 that includes the debris. For purposes of treating the ocular disorder, the debris may be removably attached on either the upper and lower eyelid margins 60, 62 or the plurality of eyelashes 64. Thereby, upon contacting the portion of the eye 15 with the debris, the swab 14 impacts the debris to remove the debris from the eye 15. Furthermore, a liquid solution configured to loosen the debris may be absorbed within the swab 14 to further aid in removing the debris from the eye 15 and/or minimizing irritation to the eye 15. It will be appreciated that any liquid solution sufficiently capable of loosening the debris to further aid in removing the debris may be so used.

The electromechanical device 10 operably drives the swab 14 to break the debris free from either of the upper or lower eyelid margins 60, 62. Further treatment may be performed to enhance the effects of the debris removal by helping to improve healing and reducing further infection of the eye 15. Such treatment may include scrubbing, exfoliating, or buffing the eyelid margin or un-roofing a meibomian gland 66 with the swab 14.

In another aspect, the cornea 58 of the eye 15 is directed away from the position of the swab 14 to minimize contacting the swab 14 to the cornea 58 during treatment. As shown in FIG. 5A, while treating the lower eyelid margin 62, the eyeball 56 directs the cornea 58 upward, thereby bringing the cornea 58 closer to the upper eyelid margin 60 than the lower eyelid margin 62. However, as shown in FIG. 5B, while treating the upper eyelid margin 60, the eyeball 56 directs the cornea 58 downward, thereby being closer to the lower eyelid margin 62 than the upper eyelid margin 60.

As shown in FIG. 5A, accessing the portion of the eye 15 with the debris, such as the upper or lower eyelid margins 60, 62, may be accomplished without further moving or lifting other portions of the eye 15. However, as shown in FIG. 5B, if accessing the portion of the eye 15 with the debris is difficult, the operator may use a hand 68, or similar gripping device, to move or lift a portion of the eye 15, such as lifting the upper or lower eyelid margin 60, 62 from against the eyeball 56, to improve access to the debris. Such lifting may be particularly beneficial for improving access to the meibomian gland 66. It will be appreciated that, in order to improve access to the debris, any portion of the eye 15 may be moved or lifted regardless of which eyelid margins 60, 62 are being treated. FIGS. 5A and 5B are merely exemplary embodiments showing both non-assisted access and assisted access of the swab 14 to the eye 15 respectively.

Furthermore, the method of treating the ocular disorder may be repeated as directed by a physician or patient in order to sufficiently remedy the disorder. For instance, in the case of physician directed treatment, the physician may direct the patient to visit the physician in periodic intervals for treating the ocular disorder with the electromechanical device 10. More specifically, the physician directs the patient to visit the physician in periodic monthly or weekly intervals so that the physician may treat the patient. In the exemplary embodiment, periodic intervals are treatments with the electromechanical device 10 once every month. It will be appreciated that any periodic interval of repeating the method of treating the ocular disorder with the electromechanical device 10 may be so used.

Alternatively, in the case of home treatment by the patient, the patient may treat his or her own ocular disorder with the electromechanical device 10 in periodic intervals. However, according to the exemplary embodiment, the physician repeats the method of treating the ocular disorder in periodic intervals with the electromechanical device 10 and the patient also treats the ocular disorder in between physician treatments using traditional treatments. This method of treating the ocular disorder with the electromechanical device 10 in treatments occurring in periodic intervals achieves superior removal of the debris compared to traditional treatments, because the periodic intervals act as reminders to the patient. Thus, the patient is less likely to forget to treat the ocular disorders once symptoms begin to subside, which may result in a resurgence of the disorder. However, the traditional treatments, despite being less effective, may be performed regularly by the patient to further treat the ocular disorder in conjunction with physician treatments with the electromechanical device 10.

In any case, the physician or patient treats the ocular disorder until the ocular disorder is sufficiently healed and thereafter to prevent a recurrence of the disorder. It will be appreciated that sufficiently healed refers to the dissipation of inflammation and/or discomfort related to the debris within the eye 15 at which time the treatments by the physician may decrease in frequency, but may continue in periodic intervals during home treatment by the patient. After each treatment, the physician or patient may remove the used instrument 22 from the chuck 32 and dispose of the used instrument 22. The used instrument 22 may then be replaced with a new instrument 22 for future treatments. In the event that the inflammation, discomfort, or debris worsens, the method of treating the ocular disorder may resume as the physician or patient desires. However, the treatment may be required in periodic intervals throughout the remainder of the patient's life.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be from such details without departing from the scope or spirit of the general inventive concept.

What is claimed is:

1. A method of treating an eye for an ocular disorder with a contact member comprising a soft and resilient material operably connected to an electromechanical device, wherein the eye has an eyelid margin and an eyeball and includes a removable debris, the method comprising:
    effecting movement of the contact member relative to the electromechanical device, the contact member having at least a portion thereof configured to access a portion of the eyelid margin, wherein the movement comprises electromechanical rotation of the contact member;
    while the contact member is being moved by the electromechanical device, contacting the eyelid margin with the contact member without lifting the eyelid margin from the eye so as to scrub the portion of the eyelid margin that includes the removable debris with the contact member thereby impacting the debris with the contact member to remove debris from the eye.

2. The method of claim 1, wherein removing debris further comprises at least one of:
    exfoliating the eyelid margin;
    unroofing a plurality of meibomian glands along the eyelid margin;
    buffing the eyelid margin; or
    breaking the debris free of the eyelid margin.

3. The method of claim 1, wherein the eye has an eyeball and further includes:
    positioning the contact member near the eyeball along the eyelid margin; and
    targeting the debris with the contact member.

4. The method of claim 1, wherein the movement of the contact member is at least one of vibrating the contact member or reciprocating the contact member.

5. The method of claim 1, further comprising repeating the effecting movement, the contacting the portion of the eye, and the impacting the debris with the contact member to remove the debris process of claim 1 after periodic intervals until the ocular disorder is sufficiently remedied.

6. The method of claim 1, wherein the contact member is a medical grade sponge for accessing the eyelid margin.

7. The method of claim 1, wherein the contact member has a length and a width, the length being between 1.0 millimeter and 2.0 millimeters and the width being between 0.5 millimeters and 1.5 millimeters for accessing an inner edge portion of the eyelid margin.

8. The method of claim 1, wherein the contact member is generally egg-shaped having an approximate length of 2.0 millimeters and an approximate width of 1.0 millimeter for accessing an inner edge portion of the eyelid margin.

9. The method of claim 1, wherein the portion of the eyelid margin includes eyelashes of the eyelid margin.

10. The method of claim 1, wherein the soft and resilient material is absorbent.

11. The method of claim 1, wherein the soft and resilient material is porous.

12. A method of treating an eye for an ocular disorder with a contact member comprising a soft and resilient material operably connected to an electromechanical device, wherein the eye has an eyelid margin and an eyeball and includes a removable debris, the method comprising:
    effecting rotational movement of the contact member relative to the electromechanical device;
    while the contact member is being moved by the electromechanical device, contacting at least a portion of the eyelid margin that includes the removable debris with the contact member without lifting the eyelid margin from the eye thereby impacting the debris with the contact member to remove debris from the eye and unroofing a plurality of meibomian glands along the eyelid margin.

13. The method of claim 12, wherein removing debris further comprises at least one of:
    scrubbing the eyelid margin;
    exfoliating the eyelid margin;
    buffing the eyelid margin; or
    breaking the debris free of the eyelid margin.

14. The method of claim 12, wherein the portion of the eyelid margin includes eyelashes of the eyelid margin.

15. The method of claim 12, and wherein the method further comprises:
    positioning the contact member near the eyeball along the eyelid margin; and
    targeting the debris with the contact member.

16. The method of claim 12, wherein the contact member is a medical grade sponge for accessing the eyelid margin.

17. The method of claim 12, wherein the soft and resilient material is absorbent.

18. The method of claim 12, wherein the soft and resilient material is porous.

* * * * *